US008895516B2

(12) United States Patent
Giannozzi et al.

(10) Patent No.: US 8,895,516 B2
(45) Date of Patent: Nov. 25, 2014

(54) MODIFIED SACCHARIDES, CONJUGATES THEREOF, AND THEIR MANUFACTURE (75) Inventors: Aldo Giannozzi, Siena (IT); Giovanni Averani, Siena (IT); Francesco Norelli, Siena (IT); Paolo Costantino, Colle Val Dielsa (IT)

(73) Assignee: Novartis AG (CH)

( * ) Notice: Subject to any disclaimer, the term of this patent is extended or adjusted under 35 U.S.C. 154(b) by 1464 days.

(21) Appl. No.: 10/526,124

(22) PCT Filed: Sep. 1, 2003

(86) PCT No.: PCT/IB03/04194
§ 371 (c)(1),
(2), (4) Date: Jun. 16, 2006

(87) PCT Pub. No.: WO2004/019992
PCT Pub. Date: Mar. 11, 2004

(65) Prior Publication Data
US 2006/0263390 A1 Nov. 23, 2006

(30) Foreign Application Priority Data

Aug. 30, 2002 (GB) .................................. 0220198.6

(51) Int. Cl.
| *A61K 31/70* | (2006.01) |
| *A61K 31/715* | (2006.01) |
| *A61K 31/7028* | (2006.01) |
| *C08B 37/00* | (2006.01) |
| *C07H 13/12* | (2006.01) |
| *A61K 47/48* | (2006.01) |

(52) U.S. Cl.
CPC ............ *C07H 13/12* (2013.01); *A61K 47/4833* (2013.01)
USPC .................. 514/23; 514/54; 514/53; 514/51; 514/25; 530/395

(58) Field of Classification Search
USPC ...................... 514/23, 54, 53, 61, 25; 530/395
See application file for complete search history.

(56) References Cited

U.S. PATENT DOCUMENTS 5,929,049 A    7/1999  Singh et al.
5,952,454 A *  9/1999  Kovac et al. .................. 528/332

FOREIGN PATENT DOCUMENTS

| EP | 447171 A2 * | 9/1991 |
| FR | 2427341 A1 * | 12/1979 |
| WO | WO 9518144 A1 * | 7/1995 |
| WO | WO 95 29927 | 11/1995 |
| WO | WO 98 31393 | 7/1998 |
| WO | 03/080678 A1 | 10/2003 |

OTHER PUBLICATIONS

Herzner et al. (Journal of Carbohydrate Chemistry (1998), 17(4&5), 759-776 (Abstract sent).*
Jujo (Yakugaku Zasshi (1943), 63, 236-9)(Abstract sent).*
Fu et al. (Gaodeng Xuexiao Huaxue Xuebao (1997), 18(7), 1071-1079) (Abstract sent).*
Cherif et al (Bioorganic & Medicinal Chemistry Letters (2002), 12(9), 1237-1240) (Abstract sent).*
Eagle et al. (Journal of Chemical Research, Synopses (1993), (10), 390) (abstract sent).*
Le Goffic et al.; FR 2427341 A1; Dec. 28, 1979 Machine, English Translation).*
STN abstract of Kurita et al. ; EP 447171 A2; Sep. 18, 1991 (abstract sent).*
STN abstract of Deninno, Michael, Paul; WO 95/18144 A1;Jul. 6, 1995 (abstract sent).*

* cited by examiner

*Primary Examiner* — Shaojia Anna Jiang
*Assistant Examiner* — Michael C Henry
(74) *Attorney, Agent, or Firm* — Helen Lee; Otis Littlefield

(57) ABSTRACT

Saccharide-protein conjugates having a new type of linker are described. The conjugates comprising the new linker are prepared from modified saccharides comprising a moiety of the formula (I): -A-N($R^1$)-L-M wherein: A is a bond, —C(O)— or —OC(O)—; R1 is selected from H or $C_1$-$C_6$ alkyl; L is a $C_1$-$C_{12}$ alkylene group; and M is a masked aldehyde group. The new linker is especially useful for preparing conjugates of *Neisseria meningitidis* serogroup A saccharide. Conjugates having this new linker have improved immunogenicity compared to other types of conjugates.

29 Claims, 3 Drawing Sheets

MODIFIED SACCHARIDES, CONJUGATES THEREOF, AND THEIR MANUFACTURE

All documents cited herein are incorporated by reference in their entirety.

RELATED APPLICATIONS

This application is the U.S. National Phase of International Application No. PCT/IB2003/004194, filed Sep. 1, 2003 and published in English, which claims priority to Great Britain Application No. GB 0220198.6, filed Aug. 30, 2002. The teachings of the above applications are incorporated herein in their entirety by reference.

TECHNICAL FIELD

The invention is in the field of saccharide chemistry and relates to modified saccharides, processes for their preparation, and conjugated derivatives. In particular, it relates to modified saccharides having a linker moiety, which may be used to link the saccharide to a protein.

BACKGROUND ART

Polysaccharides are important biological molecules and they have been widely used in the pharmaceutical industry for the prevention and treatment of diseases. For example, capsular polysaccharides have been used for many years in vaccines against capsulated bacteria, such as meningococcus (*Neisseria meningitidis*), pneumococcus (*Streptococcus pneumoniae*) and Hib (*Haemophilus influenzae* type B).

To enhance immunogenicity of these polysaccharides, particularly in children, conjugate vaccines were developed. These comprise a capsular polysaccharide conjugated to a carrier protein [e.g. U.S. Pat. Nos. 4,711,779, 4,761,283 and 4,882,317]. The conjugated molecule may have the polysaccharide and protein linked directly or the polysaccharide and protein may be linked via a linker moiety.

Whilst different types of linker moieties have been developed, there is a need for new types of linker which are versatile and which can be coupled to the polysaccharide and protein using simple, reliable chemistry. There is a further need for new linkers which are non-toxic and which can be formed under mild conditions, avoiding the use of harsh reagents, such as strong acids and bases.

DISCLOSURE OF THE INVENTION

Modified Saccharides of the Invention

The invention provides a modified capsular saccharide comprising a moiety of the formula (I):

-A-N(R$^1$)-L-M    (I)

wherein:
A is a bond, —C(O) or —OC(O)—
R$^1$ is selected from H or $C_1$-$C_6$ alkyl;
L is a $C_1$-$C_{12}$ alkylene group;
M is a masked aldehyde group.

The term "modified capsular saccharide" means a saccharide which is obtainable from a native capsular saccharide by suitable modification. Hence, the basic sequence of repeating monosaccharide units in the native capsular saccharide is retained in the modified capsular saccharides of the present invention.

The term "saccharide" encompasses both oligosaccharides (e.g. containing from 2 to 39 monosaccharide units) and polysaccharides (e.g. containing 40 or more monosaccharide units). As found naturally in bacteria, native capsular saccharides generally take the form of polysaccharides. Polysaccharides may be manipulated to give shorter oligosaccharides. Oligosaccharides may be obtained by purification and/or sizing of the native polysaccharide (e.g. by hydrolysis in mild acid, by heating, by sizing chromatography, etc.).

Typically, the modified saccharides of the present invention are oligosaccharides. Oligosaccharides may be obtained from polysaccharides by any of the sizing methods described above.

The modified capsular saccharides of this invention are obtainable from native capsular saccharides. However, the present invention is not limited to modified saccharides obtained from native capsular saccharides. The modified capsular saccharides of the present invention may be obtained by other methods, such as total or partial synthesis.

In the modified capsular saccharides of the present invention, the moiety of formula (I) may be derived from a non-terminal hydroxyl group of a capsular saccharide or from a terminal anomeric hydroxyl group of a capsular saccharide.

When the moiety of formula (I) is derived from an anomeric hydroxyl group, it preferably replaces the anomeric hydroxyl group by, for example, a reductive amination reaction. Reductive amination reactions on terminal hydroxyl groups are well known in the art.

When the moiety of formula (I) is derived from a non-terminal hydroxyl group, it is preferably linked to the non-terminal hydroxyl group via, for example, a carbamate group. Hence, in a preferred embodiment, the modified capsular saccharide of the present invention comprises a moiety of the formula (Ia):

—OC(O)N(R$^1$)-L-M    (Ia)

wherein R$^1$, L and M are as defined above.

Such compounds may be prepared by derivatizing a free hydroxyl group on a saccharide with, for example, CDI and then reacting the carbamate intermediate with an amine of formula: HN(R$^1$)-L-M.

Preferably, R$^1$ is H. Preferably, L is a $C_1$-$C_6$ alkylene group. More preferably L is —$CH_2CH_2CH_2$—. The L group acts as a spacer when the moiety of formula (I) is used to link a capsular saccharide to a protein in a saccharide-protein conjugate. It is found that a spacer group between the saccharide and the protein improves the stability of the conjugate.

The skilled person will be aware of many different functionalities which may be readily converted into an aldehyde group. Any such functionality would be suitable as the masked aldehyde group M. Preferably, the masked aldehyde group M is selected from wherein:
R² is selected from H, $C_1$-$C_{12}$ alkyl, $C_3$-$C_{12}$ cycloalkyl, $C_5$-$C_{12}$ aryl or $C_{5-12}$ aryl-$C_{1-6}$ alkyl (preferably R² is not H);

X and Y are the same or different and are independently selected from O or S;

R³ and R⁴ are independently selected from $C_1$-$C_{12}$ alkyl, $C_3$-$C_{12}$ cycloalkyl, $C_5$-$C_{12}$ aryl or $C_{5-12}$ aryl-$C_{1-6}$ alkyl; or R³ and R⁴ are joined to form a $C_3$, $C_4$, $C_5$, $C_6$, $C_7$ or $C_8$ cycloalkyl ring containing the heteroatoms X and Y;

R⁵ and R⁶ are independently selected from H, $C_1$-$C_{12}$ alkyl, $C_3$-$C_{12}$ cycloalkyl, $C_5$-$C_{12}$ aryl or $C_{5-12}$ aryl-$C_{1-6}$ alkyl; or R⁵ and R⁶ are joined to form a $C_3$ or $C_{12}$ cycloalkyl ring;

R⁹ and R¹⁰ are independently selected from H, $C_1$-$C_{12}$ alkyl, $C_3$-$C_{12}$ cycloalkyl, $C_5$-$C_{12}$ aryl or $C_{5-12}$ aryl-$C_{1-6}$ alkyl; or R⁹ and R¹⁰ are joined to form a $C_{3-12}$ cycloalkyl ring; and R⁷ and R⁸ are independently selected from $C_1$-$C_{12}$ alkyl or $C_3$-$C_{12}$ cycloalkyl groups.

The term "alkyl" is used herein to refer to alkyl groups in both straight and branched forms, The alkyl group may be interrupted with 1, 2 or 3 heteroatoms selected from —O—, —NH— or —S—. The alkyl group may also be interrupted with 1, 2 or 3 double and/or triple bonds. However, the term "alkyl" usually refers to alkyl groups having no heteroatom interruptions or double or triple bond interruptions. Where reference is made to $C_{1-12}$ alkyl, it is meant the alkyl group may contain any number of carbon atoms between 1 and 12 (e.g. $C_1$, $C_2$, $C_3$, $C_4$, $C_5$, $C_6$, $C_7$, $C_8$, $C_9$, $C_{10}$, $C_{11}$, $C_{12}$). Similarly, where reference is made to $C_1$— alkyl, it is meant the alkyl group may contain any number of carbon atoms between 1 and 6 (e.g. $C_1$, $C_2$, $C_3$, $C_4$, $C_5$, $C_6$).

The term "alkylene" is used herein to refer to alkylene groups in both straight and branched forms, The alkylene group may be interrupted with 1, 2 or 3 heteroatoms selected from —O—, —NH— or —S—. The alkylene group may also be interrupted with 1, 2 or 3 double and/or triple bonds. However, the term "alkylene" usually refers to alkylene groups having no heteroatom interruptions or double or triple bond interruptions. Where reference is made to $C_{1-12}$ alkylene, it is meant the alkylene group may contain any number of carbon atoms between 1 and 12 (e.g. $C_1$, $C_2$, $C_3$, $C_4$, $C_5$, $C_6$, $C_7$, $C_8$, $C_9$, $C_{10}$, $C_{11}$, $C_{12}$). Similarly, where reference is made to $C_{1-6}$ alkylene, it is meant the alkylene group may contain any number of carbon atoms between 1 and 6 (e.g. $C_1$, $C_2$, $C_3$, $C_4$, $C_5$, $C_6$).

The term "cycloalkyl" includes cycloalkyl, polycycloalkyl, and cycloalkenyl groups, as well as combinations of these with alkyl groups, such as cycloalkylalkyl groups. The cycloalkyl group may be interrupted with 1, 2 or 3 heteroatoms selected from —O—, —NH— or —S—. However, the term "cycloalkyl" usually refers to cycloalkyl groups having no heteroatom interruptions. Examples of cycloalkyl groups include cyclopentyl, cyclohexyl, cyclohexenyl, cyclohexylmethyl and adamantyl groups. Where reference is made to $C_{3-12}$ cycloalkyl, it is meant that the cycloalkyl group may contain any number of carbon atoms between 3 and 12 (e.g. $C_3$, $C_4$, $C_5$, $C_6$, $C_7$, $C_8$, $C_9$, $C_{10}$, $C_{11}$, $C_{12}$).

The term "aryl" is used herein to refer to a carbon and hydrogen-containing aromatic group, such as phenyl or naphthyl. Where reference is made to $C_{5-12}$ aryl, it is meant that the aryl group may contain any number of carbon atoms between 5 and 12 (e.g. $C_5$, $C_6$, $C_7$, $C_8$, $C_9$, $C_{10}$, $C_{11}$, $C_{12}$).

The term "$C_{5-12}$ aryl-$C_{1-6}$ alkyl" refers to groups such as benzyl, phenylethyl and naphthylmethyl.

Preferably, the masked aldehyde is —CH(OH)CH₂OH. Preferably, the modified capsular saccharide of the present invention comprises a moiety of formula —NH(CH₂)₃CH(OH)CH₂OH, more preferably —OC(O)NH(CH₂)₃CH(OH)CH₂OH.

The present invention provides compounds having a masked aldehyde group. The use of a masked aldehyde advantageously prevents unwanted side reactions during modification of the capsular saccharide. Moreover, when an aldehyde group is revealed, it may be used for reductive amination coupling with, for example, an amino group on a protein.

Generally, the moiety of formula (I) or (Ia) performs the function of providing a handle for subsequent reaction with an amine group of a protein. Hence, the moiety of formula (I) or (Ia) is usually used to form a linker group in a saccharide-protein conjugate.

However, the moiety of formula (I) or (Ia), preferably (Ia), may be used as a blocking group to stabilise the saccharide against degradation, especially degradation by acid hydrolysis. This further use of the moiety of formula (Ia) may be as an alternative to or in addition to its use as a linker group. The use of blocking groups to stabilise capsular saccharides is described in international patent application PCT/IB03/01436.

When the moiety of formula (Ia) is used as a stabilizing blocking group, the modified saccharide preferably has more than one of these moieties to provide a stabilizing effect. For example, all or substantially all the monosaccharide units in the modified saccharide may have a blocking group comprising a group of formula (Ia). Alternatively, at least 10%, 20%, 30%, 40%, 50%, 60%, 70%, 80% or 90% of the monosaccharide units may have a blocking group comprising a group of formula (I). At least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 monosaccharide units in the modified saccharide may have blocking groups.

Likewise, the number of blocking groups on each monosaccharide unit may vary. For example, the number of blocking groups on a monosaccharide unit may be 1, 2, 3, 4, 5 or 6, preferably 1 to 4, and more preferably 1 or 2.

Preferably, the modified saccharide of the present invention comprises a moiety of formula (I) or (Ia) which is then converted to an aldehyde. Hence, the present invention further provides a modified saccharide comprising a moiety of formulae (II) or, preferably, (IIa):

-A-N(R¹)-L-C(O)H    (II)

—OC(O)N(R¹)-L-C(O)H    (IIa)

wherein A, R¹ and L are as defined above.

The conversion of masked aldehydes of formula (I) or (Ia) into aldehydes of formula (II) or (IIa) involves a simple synthetic step. For example, diols may be converted to aldehydes by oxidative cleavage (e.g. NaIO₄, Pb(OAc)₄, etc.); alcohols may be converted to aldehydes by oxidation (e.g. Swern oxidation, Dess-Martin oxidation, $Cr^{VI}$ oxidations, etc.); alkenes may be converted to aldehydes by oxidative double bond cleavage (e.g. ozonolysis followed by reductive work up, OsO₄/NaIO₄, OsO₄/Pb(OAc)₄, etc.); acetals may be converted to aldehydes by acid hydrolysis; thioacetals may be converted to aldehydes by metal coordination, alkylation or oxidation (e.g. $Hg^{II}$, $Ag^{I}$, $Ag^{II}$, $Cu^{II}$, MeI, N-bromosuccinimide, etc.); carboxylic esters, cyano compounds and Weinreb amides may be converted to aldehydes by a suitable reduction (e.g. NaBH₄, DIBAL, etc.).

Preferably, the masked aldehyde M is of formula —CH(OH)CH₂OH. This diol may be advantageously converted to the corresponding aldehyde using a mild periodate oxidizing agent. It has been found that periodate oxidants, such as NaIO₄, selectively form an aldehyde without affecting other sensitive functionalities on the capsular saccharide.

Hence, in a preferred embodiment, the modified saccharide comprises a moiety of formula: —NH(CH₂)₃C(O)H, more preferably —OC(O)NH(CH₂)₃C(O)H.

Saccharide-Protein Conjugates

The modified saccharide comprising a moiety of formula (II) or (IIa) may be used to couple the saccharide to a protein carrier. The coupling is preferably via reductive amination of an amino group on the protein with the aldehyde group on the modified saccharide comprising a moiety of formula (II) or (IIa). Reductive amination reactions are well known to be a reliable method for coupling saccharides and proteins. Usually, the reaction is performed using NaBH₃CN, although other suitable reductants may also be used.

Accordingly, the present invention provides a saccharide-protein conjugate wherein the saccharide and protein moieties are linked via a group of formula (IV) or, preferably, (IVa):

wherein A, R¹ and L are as defined above. Preferably, L is —(CH₂)₄— in conjugates of the present invention. In a preferred embodiment, the saccharide and protein moieties are linked by a group of formula: —OC(O)NH—(CH₂)₄—NH—. The —NH— will typically be derived from an existing amine group on the protein, e.g. in a lysine residue.

In the protein-saccharide conjugates of the present invention, the protein is preferably a bacterial toxin or toxoid, more preferably a diphtheria or tetanus toxin or toxoid. These are commonly used in conjugate vaccines. The CRM₁₉₇ diphtheria toxoid is particularly preferred [1]. Other suitable carrier proteins include the *N. meningitidis* outer membrane protein [2], synthetic peptides [3,4], heat shock proteins [5,6], pertussis proteins [7,8], protein D from *H. influenzae* [9], cytokines [10], lympholines [10], hormones [10], growth factors [10], toxin A or B from *C. difficile* [11], iron-uptake proteins [12], etc. It is possible to use mixtures of carrier proteins.

After conjugation, free and conjugated saccharides can be separated. There are many suitable methods, including hydrophobic chromatography, tangential ultrafiltration, diafiltration, etc. [see also refs. 13, 14, etc.].

A single carrier protein may carry multiple different saccharides [15].

Modified *Neisseria meningitidis* Serogroup A Saccharides

In all the embodiments described above, the modified capsular saccharide is preferably a modified *Neisseria meningitidis* saccharide. More preferably, the modified capsular saccharide is a modified *Neisseria meningitidis* serogroup A saccharide.

The *Neisseria meningitidis* serogroup A saccharide has the following structure:

Accordingly, the present invention provides a saccharide of formula:

wherein:

T is of the formula (A) or (B):

(A)

(B)

n is an integer from 1 to 100;

each Z group is independently selected from —OH, —OAc, —OC(O)N($R^1$)-L-M or —OC(O)N($R^1$)-L-C(O)H;

each Q group is independently selected from —OH, —OAc, —OC(O)N($R^1$)-L-M or —OC(O)N($R^1$)-L-C(O)H;

W is selected from —OH, —OAc, —OC(O)N($R^1$)-L-M or —OC(O)N($R^1$)-L-C(O)H (preferably W is OH);

V is —N($R^1$)-L-M or —N(W)— L-C(O)H;

wherein $R^1$, L and M are as defined above, and provided that the saccharide comprises at least one moiety of the formula —N($R^1$)-L-M, —N($R^1$)-L-C(O)H, —OC(O)N($R^1$)-L-M or —OC(O)N($R^1$)-L-C(O)H.

Preferably, n is an integer from 15 to 25.

Preferably, T is of the formula (A). Preferably the saccharide comprises at least one moiety of the formula —OC(O)N ($R^1$)-L-M or —OC(O)N($R^1$)-L-C(O)H.

Preferably, Q and Z are a mixture of OH and OAc groups in essentially the same relative proportions as in the native *Neisseria meningitidis* serogroup A saccharide, with the exception that one of the Q or Z groups, preferably one of the Q groups, is —OC(O)N($R^1$)-L-M or —OC(O)N($R^1$)-L-C(O)H.

Process for Producing Modified Saccharides

Figure 1:
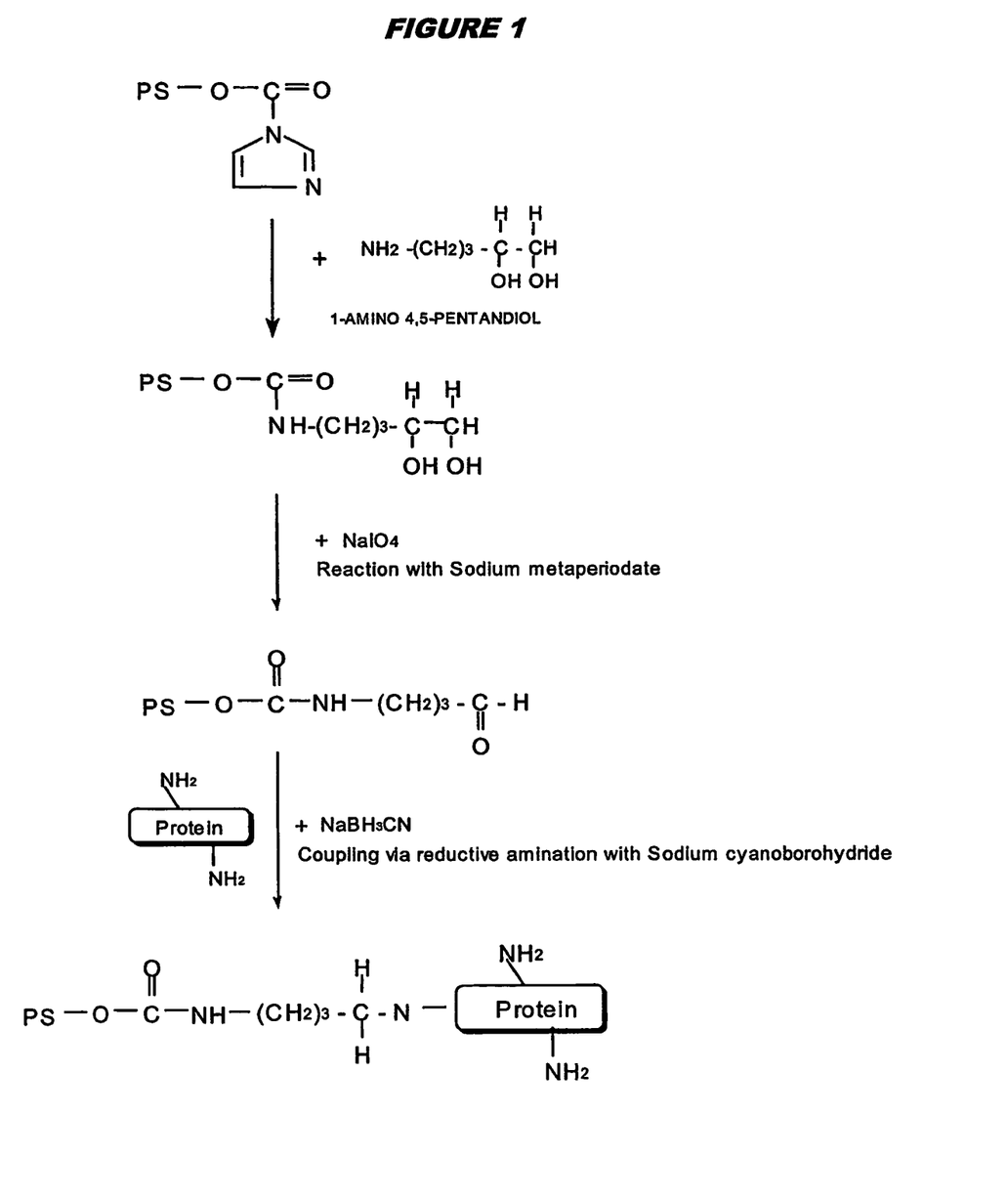
FIG. 1 shows the synthesis of a saccharide-protein conjugate from a CDI-activated saccharide.
Figure 2:
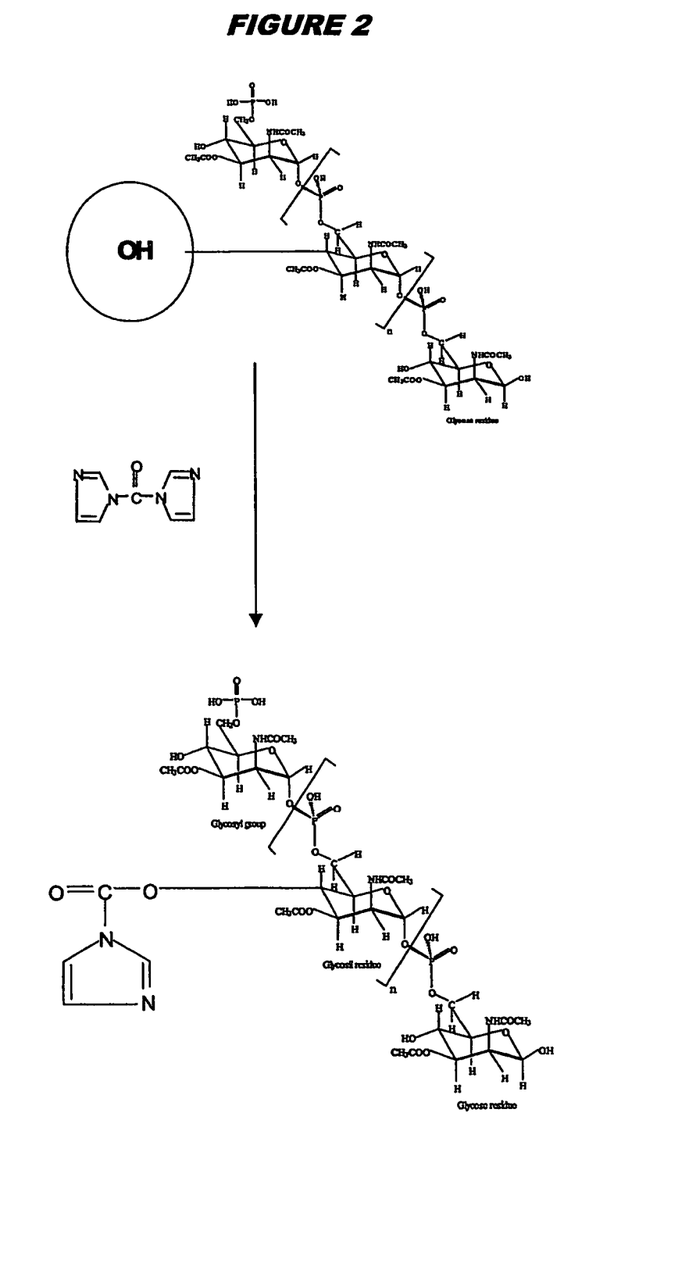
FIG. 2 shows the reaction of a hydroxyl group on a Neisseria meningitidis serogroup A saccharide with CDI.

This invention further provides a process for modifying a capsular saccharide comprising the steps of:
(a) providing a capsular saccharide having a hydroxyl group;
(b) reacting the hydroxyl group with a bifunctional reagent in an organic solvent;

(c) reacting the product of step (b) with an amino compound of formula (III):

$$HN(R^1)\text{-}L\text{-}M \quad (III)$$

wherein $R^1$, L and M are as defined above.

The capsular saccharide may be a native capsular saccharide (oligosaccharide or polysaccharide). Alternatively, the capsular saccharide may be, for example, a de-O-acetylated capsular saccharide, a blocked capsular saccharide (as described in PCT/IB03/01436) or a capsular saccharide having a terminal amino group (e.g. obtained by reductive amination).

The term "bifunctional reagent" means any reagent which is capable of performing the dual functions of (i) providing a first electrophilic carbon atom for coupling with the hydroxyl group(s) on the saccharide; and (ii) providing a second electrophilic carbon atom for coupling with the amino group used in step (b2). Generally, the second electrophilic carbon atom is regenerated from the first electrophilic carbon atom during step (b). The bifunctional reagent provides a —C(O)— linkage between the polysaccharide and the amino compound.

Bifunctional reagents for use in the present invention include, but are not limited to, 1,1'-carbonyldiimidazole (CDI), carbonyl di-1,2,4-triazole (CDT), carbonyl di-1,2,3-benzotriazole (CDB), diphenylcarbonate, cyanogen bromide, phosgene or triphosgene. The skilled person will be aware of other bifunctional reagents which can perform the same function as these. CDI is preferred, because it is a particularly mild reagent and avoids generating strongly acidic gases, such as HCl or HBr.

Preferably, the organic solvent is an aprotic solvent Aprotic solvents are well known to the person skilled in the art and do not contain any ionizable hydrogen atoms. These solvents are advantageous because they facilitate the reaction of hydroxyl group(s) on the saccharide with the bifunctional reagent, by enhancing the nucleophilicity of the hydroxyl group(s). Suitable aprotic solvents include, but are not limited to dimethylsulfoxide (DMSO), dimethylformamide (DMF), formamide, hexamethylphosphoramide (HMPA), hexamethylphosphorus triamide (HMPT), 1,3-dimethyl-3,4,5,6-tetrahydro-2(1H)-pyrimidinone (DMPU) or dimethylacetamide (DMAC). DMSO is preferred.

In step (c) above, the intermediate carbamate compound generated after step (b) is reacted with an amine of formula (III). Preferably, the amine of formula (III) is the tris-nucleophile $H_2N(CH_2)CH(OH)CH_2OH$.

A preferred process of the present invention is exemplified in Scheme 1 below:

Scheme 1

Sacc = saccharide moiety

In Scheme 1, the saccharide (e.g. Men A polysaccharide or oligosaccharide) is first activated through one of its hydroxyl groups using CDI in DMSO solvent. The resulting imidazole carbamate is trapped by the tris-nucleophile $H_2N(CH_2)_3CH(OH)CH_2OH$ to afford the modified saccharide having a masked aldehyde functionality. FIG. 2 shows the activation step for a *Neisseria meningitidis* serogroup A saccharide The modified saccharides may alternatively be prepared in a one-step process by reacting one or more hydroxyl groups on a capsular saccharide with a reagent of formula XC(O)N ($R^1$)-L-M, wherein X is a leaving group and $R^1$, L and M are as defined above. Suitable leaving groups include, but are not limited to, —Cl, —Br, —$CF_3$, —$OC_6H_5$ or —$CCl_3$.

In a preferred embodiment, there is provided a process for modifying a saccharide as described above which further comprises the steps of (d) unmasking the masked aldehyde group M, thereby providing an aldehyde compound; and (e)

linking the aldehyde compound to a protein by a reductive amination reaction. In this process, the masked aldehyde group M is preferably —CH(OH)CH$_2$OH, the unmasking step is preferably a periodate cleavage, and the reducing agent in the reductive amination reaction is preferably NaBH$_3$CN. This preferred embodiment is shown in FIG. 1. In FIG. 1, PS represents a polysaccharide or oligosaccharide derived from native *Neisseria meningitidis* serogroup A saccharide.

Pharmaceutical Compositions and Methods

The invention provides a pharmaceutical composition comprising (a) a modified saccharide of the invention and/or a conjugate of the invention, and (b) a pharmaceutically acceptable carrier.

Where a conjugate is present, the composition may also comprise free carrier protein [16].

'Pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, trehalose [17] lipid aggregates (such as oil droplets or liposomes), and inactive virus particles. Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. A thorough discussion of pharmaceutically acceptable excipients is available in Remington's Pharmaceutical Sciences e.g. the 2000 edition (ISBN: 0683306472).

Typically, the compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. Direct delivery of the compositions will generally be parenteral (e.g. by injection, either subcutaneously, intraperitoneally, intravenously or intramuscularly, or delivered to the interstitial space of a tissue). The compositions can also be administered into a lesion. Other modes of administration include oral and pulmonary administration, rectal (suppositories), and transdermal or transcutaneous applications [e.g. ref. 18], needles, and hyposprays. Dosage treatment may be a single dose or a multiple dose schedule (e.g. including booster doses).

The composition of the invention is preferably sterile, buffered, and/or pyrogen-free.

The composition is preferably an immunogenic composition (e.g. a vaccine). Vaccines based on saccharides or saccharide-protein conjugates are well known in the art.

Immunogenic compositions comprise an immunologically effective amount of saccharide antigen, as well as any other of other specified components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The vaccine may be administered in conjunction with other immunoregulatory agents.

The immunogenic composition may include an adjuvant. Preferred adjuvants to enhance effectiveness of the composition include, but are not limited to: (A) aluminium compounds (e.g. aluminium hydroxide, aluminium phosphate, aluminium hydroxyphosphate, oxyhydroxide, orthophosphate, sulphate, etc. [e.g. see chapters 8 & 9 of ref. 19]), or mixtures of different aluminium compounds, with the compounds taking any suitable form (e.g. gel, crystalline, amorphous, etc.), and with adsorption being preferred; (B) MF59 (5% Squalene, 0.5% Tween 80, and 0.5% Span 85, formulated into submicron particles using a microfluidizer) [see Chapter 10 of ref 19; see also ref. 20]; (C) liposomes [see Chapters 13 and 14 of ref. 19]; (D) ISCOMs [see Chapter 23 of ref. 19], which may be devoid of additional detergent [21]; (E) SAF, containing 10% Squalane, 0.4% Tween 80, 5% pluronic-block polymer L121, and thr-MDP, either microfluidized into a submicron emulsion or vortexed to generate a larger particle size emulsion [see Chapter 12 of ref. 19]; A) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (G) saponin adjuvants, such as QuilA or QS21 [see Chapter 22 of ref 19], also known as Stimulon™; (H) chitosan [e.g. 22]; (I) complete Freund's adjuvant (CFA) and incomplete Freund's adjuvant (IFA); (J) cytokines, such as interleukins (e.g. IL-1, IL-2, IL-4, IL-5, IL-6, IL-7, IL-12, etc.), interferons (e.g. interferon-γ), macrophage colony stimulating factor, tumor necrosis factor, etc. [see Chapters 27 & 28 of ref. 19]; (K) microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.); (L) monophosphoryl lipid A (MPL) or 3-O-deacylated MPL (3dMPL) [e.g. chapter 21 of ref. 19]; (M) combinations of 3dMPL with, for example, QS21 and/or oil-in-water emulsions [23]; (N) oligonucleotides comprising CpG motifs [24] i.e. containing at least one CG dinucleotide, with 5-methylcytosine optionally being used in place of cytosine; (O) a polyoxyethylene ether or a polyoxyethylene ester [25]; (P) a polyoxyethylene sorbitan ester surfactant in combination with an octoxynol [26] or a polyoxyethylene alkyl ether or ester surfactant in combination with at least one additional non-ionic surfactant such as an octoxynol [27]; (O) an immunostimulatory oligonucleotide (e.g. a CpG oligonucleotide) and a saponin [28]; (R) an immunostimulant and a particle of metal salt [29]; (S) a saponin and an oil-in-water emulsion [30]; (T) a saponin (e.g. QS21)+3dMPL+IL-12 (optionally+a sterol) [31]; (U) *E. coli* heat-labile enterotoxin ("LT"), or detoxified mutants thereof, such as the K63 or R72 mutants [e.g. Chapter 5 of ref. 32]; (V) cholera toxin ("CT"), or detoxified mutants thereof [e.g. Chapter 5 of ref. 32]; (W) double-stranded RNA; (X) monophosphoryl lipid A mimics, such as aminoalkyl glucosaminide phosphate derivatives e.g. RC-529 [33]; (Y) polyphosphazene (PCPP); or (Z) a bioadhesive [34] such as esterified hyaluronic acid microspheres [35] or a mucoadhesive selected from the group consisting of cross-linked derivatives of poly(acrylic acid), polyvinyl alcohol, polyvinyl pyrollidone, polysaccharides and carboxymethylcellulose. Other substances that act as immunostimulating agents to enhance the effectiveness of the composition [e.g. see Chapter 7 of ref. 19] may also be used. Aluminium salts (especially aluminium phosphates and/or hydroxides) are preferred adjuvants for parenteral immunisation. Mutant toxins are preferred mucosal adjuvants.

Muramyl peptides include N-acetyl-muramyl-L-threonyl-D-isoglutamine (thr-MDP), N-acetylnormuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine MTP-PE), etc.

Once formulated, the compositions of the invention can be administered directly to the subject. The subjects to be treated can be animals; in particular, human subjects can be treated. The vaccines are particularly useful for vaccinating children and teenagers.

Vaccines according to the invention may either be prophylactic (i.e. to prevent infection) or therapeutic (i.e. to treat disease after infection), but will typically be prophylactic.

As well as modified saccharides, the composition may comprise further antigenic components. For instance, the composition may include one or more further saccharides (whether or not modified according to the invention). For instance, the composition may comprise saccharides from serogroups C, W135 and Y of *N. meningitidis* (e.g. in addition to a modified MenA saccharide). These will typically be conjugated to carrier proteins, and saccharides from different serogroups of *N. meningitidis* may be conjugated to the same or different carrier proteins. Where a mixture comprises capsular saccharides from both serogroups A and C, it is preferred that the ratio (w/w) of MenA saccharide:MenC saccharide is greater than 1 (e.g. 2:1, 3:1, 4:1, 5:1, 10:1 or higher). Improved immunogenicity of the MenA component has been observed when it is present in excess (mass/dose) to the MenC component.

The composition may also comprise protein antigens.

Antigens which can be included in the composition of the invention include:
- antigens from *Helicobacter pylori* such as CagA [36 to 39], VacA [40, 41], NAP [42, 43, 44], HopX [e.g. 45], HopY [e.g. 45] and/or urease.
- a protein antigen from *N. meningitidis* serogroup B, such as those in refs. 46 to 52, with protein '287' (see below) and derivatives (e.g. 'ΔG287') being particularly preferred.
- an outer-membrane vesicle (OMV) preparation from *N. meningitidis* serogroup B, such as those disclosed in refs. 53, 54, 55, 56, etc.
- a saccharide antigen from *N. meningitidis* serogroup C, such as the oligosaccharide disclosed in ref. 57 from serogroup C [see also ref. 58].
- a saccharide antigen from *Streptococcus pneumoniae* [e.g. 59, 60, 61].
- an antigen from hepatitis A virus, such as inactivated virus [e.g. 62, 63].
- an antigen from hepatitis B virus, such as the surface and/or core antigens [e.g. 63, 64].
- an antigen from hepatitis C virus [e.g. 65].
- an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 66 & 67].
- a diphtheria antigen, such as a diphtheria toxoid [e.g. chapter 3 of ref. 68] e.g. the $CRM_{197}$ mutant [e.g. 69].
- a tetanus antigen, such as a tetanus toxoid [e.g. chapter 4 of ref. 68].
- a saccharide antigen from *Haemophilus influenzae* B [e.g. 58].
- an antigen from *N. gonorrhoeae* [e.g. 46, 47, 48].
- an antigen from *Chlamydia pneumoniae* [e.g. 70, 71, 72, 73, 74, 75, 76].
- an antigen from *Chiamydia trachomatis* [e.g. 77].
- an antigen from *Porphyromonas gingivalis* [e.g. 78].
- polio antigen(s) [e.g. 79, 80] such as IPV or OPV.
- rabies antigen(s) [e.g. 81] such as lyophilised inactivated virus [e.g. 82, RabAvert™].
- measles, mumps and/or rubella antigens [e.g. chapters 9, 10 & 11 of ref. 68].
- influenza antigen(s) [e.g. chapter 19 of ref. 68], such as the haemagglutinin and/or neuraminidase surface proteins.
- an antigen from *Moraxella catarrhalis* [e.g. 83].
- an antigen from *Streptococcus agalactiae* (group B streptococcus) [e.g. 84, 85].
- a saccharide antigen from *Streptococcus agalactiae* (group B streptococcus).
- an antigen from *Streptococcus pyogenes* (group A streptococcus) [e.g. 85, 86, 87].
- an antigen from *Staphylococcus aureus* [e.g. 88].
- an antigen from *Bacillus anthracis* [e.g. 89, 90, 91].
- an antigen from a virus in the flaviviridae family (genus flavivirus), such as from yellow fever virus, Japanese encephalitis virus, four serotypes of Dengue viruses, tick-borne encephalitis virus, West Nile virus.
- a pestivirus antigen, such as from classical porcine fever virus, bovine viral diarrhoea virus, and/or border disease virus.
- a parvovirus antigen e.g. from parvovirus B19.
- a prion protein (e.g. the CJD prion protein)
- an amyloid protein, such as a beta peptide [92]
- a cancer antigen, such as those listed in Table 1 of ref. 93 or in tables 3 & 4 of ref. 94.

The composition may comprise one or more of these further antigens.

Toxic protein antigens may be detoxified where necessary (e.g. detoxification of pertussis toxin by chemical and/or genetic means [67]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens are preferably adsorbed to an aluminium salt.

Antigens in the composition will typically be present at a concentration of at least 1 µg/ml each. In general, the concentration of any given antigen will be sufficient to elicit an immune response against that antigen.

As an alternative to using proteins antigens in the composition of the invention, nucleic acid encoding the antigen may be used [e.g. refs. 95 to 103]. Protein components of the compositions of the invention may thus be replaced by nucleic acid (preferably DNA e.g. in the form of a plasmid) that encodes the protein.

The invention also provides a method for raising an antibody response in a mammal, comprising administering a pharmaceutical composition of the invention to the mammal. The mammal is preferably a human. The human may be an adult or, preferably, a child. The antibody response is preferably protective against infection by *N. meningitidis* serogroup A.

The invention also provides a method for immunising a mammal, comprising administering a pharmaceutical composition of the invention to the mammal.

This invention also provides a modified saccharide of the invention, or a conjugate of the invention, for use as a medicament.

The invention also provides the use of a modified saccharide of the invention, or of a conjugate of the invention, in the manufacture of a medicament for preventing or treating a disease caused by capsulate bacteria Diseases caused by Neisseria include meningitis, septicaemia and gonorrhoea. Diseases caused by H. influenzae include otitis media, bronchitis, pneumonia, cellulitis, pericarditis, and meningitis. Diseases caused by pneumococcus include meningitis, sepsis and pneumonia. The prevention and/or treatment of bacterial meningitis is thus preferred.

MODES FOR CARRYING OUT THE INVENTION

Comparative Immunogenicity Studies

The present invention provides an improved type of linkage between a saccharide and a protein. In addition, it was found that saccharide-protein conjugates according to the present invention have improved immunogenicity compared to other types of saccharide-protein conjugates.

For the purposes of comparison, a saccharide-protein conjugate having an alternative linkage was prepared. A modified Neisseria meningitidis serogroup A polysaccharide was prepared by CDI-activation of a hydroxyl group on the saccharide, following by quenching of the CDI carbamate intermediate with $NH_2-(CH_2)_5-CO_2H$. This modified polysaccharide was used to prepare a saccharide-protein conjugate by EDAC-activated coupling of the carboxyl group with $CRM_{197}$. Hence, the polysaccharide and $CRM_{197}$ were coupled via the linker group $-OC(O)NH-(CH_2)_5-C(O)NH-$. For the purposes of this comparative study, this method of preparing a saccharide-protein conjugate is called "the carbodiimide method".

The saccharide-protein conjugate prepared by the carbodiimide method was compared with a saccharide-protein conjugate according to the present invention. Hence, a modified Neisseria meningitidis serogroup A polysaccharide was prepared by CDI-activation of a hydroxyl group on the polysaccharide, followed by quenching of the CDI carbamate intermediate with the tris-nucleophile $NH_2-(CH_2)_3-CH(OH)CH_2OH$. Following periodate cleavage to reveal an aldehyde, the modified polysaccharide was coupled to $CRM_{197}$ by reductive amination (as illustrated in FIG. 1). Hence, the polysaccharide and $CRM_{197}$ were coupled via the linker group $-OC(O)NH-(CH_2)_4-NH-$. For the purposes of this comparative study, this method of preparing a saccharide-protein conjugate is called "the reductive amination method".

The immunogenicities of conjugates prepared by the carbodiimide method and the reductive amination method (at two different ratios) were determined in Balb/c mice. The conjugates were administered as two doses (0 & 14 days) of 2 μg/dose (expressed as mass of saccharide). A bleeding was taken on day 25 and IgG titres (GMT) were determined. In addition, serum bactericidal antibody (SBA) titres against MenA strain F8238 were assessed. For comparison, an oligosaccharide conjugate of the invention and unconjugated polysaccharide were also tested.

Figure 3:
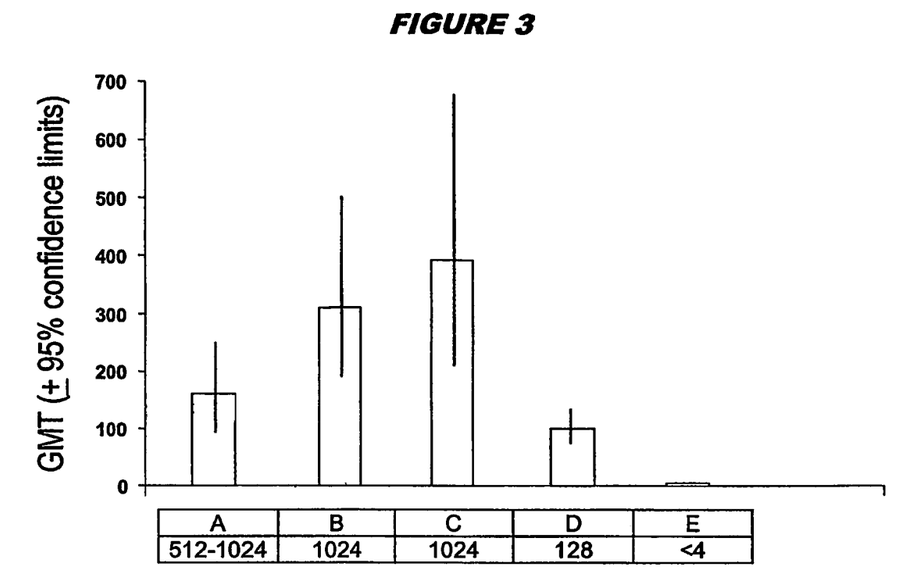
FIG. 3 shows the results of comparative immunogenicity studies. The graph shows GMT values for five different saccharide immunogens (A) to (E), and the table shows serum bactericidal titres against the serogroup A strain F8238.

Results are shown in FIG. 3. The oligosaccharide conjugate (C) gave the best GMT value and a SBA titre of 1024. In contrast, plain polysaccharide (E) gave a poor GMT titre (comparable to saline control) and poor SBA titre (<4). When conjugated to CRM197 using the cardbodiimide method (D), both titres increased (SBA: 128). When conjugated to CRM197 using the reductive amination method (A and B), GMT and SBA titres increased (SBA: between 512 and 1024). The SBA titre achieved with the conjugate prepared using the reductive amination matched that of the conjugated oligosaccharide.

A comparative ELISA schedule using a guinea pig model confirmed the results obtained with the Balb/C mice.

It will be understood that the invention is described above by way of example only and modifications may be made whilst remaining within the scope and spirit of the invention.

REFERENCES (THE CONTENTS OF WHICH ARE INCORPORATED HEREIN IN FULL)

[1] Research Disclosure, 453077 (January 2002)
[2] EP-A-0372501
[3] EP-A-0378881
[4] EP-A-0427347
[5] WO93/17712
[6] WO94/03208
[7] WO98/58668
[8] EP-A-0471177
[9] WO00/56360
[10] WO91/01146
[11] WO00/61761
[12] WO01/72337
[13] Lei et al. (2000) Dev Biol (Basel) 103:259-264
[14] WO00/38711
[15] WO99/42130
[16] WO96/40242
[17] WO00/56365
[18] WO98/20734
[19] Vaccine design: the subunit and adjuvant approach, eds. Powell & Newman, Plenum Press 1995 (ISBN 0-306-44867-X).
[20] WO90/14837.
[21] WO00/07621.
[22] WO99/27960.
[23] European patent applications 0835318, 0735898 and 0761231.
[24] Krieg (2000) Vaccine 19:618-622; Kreg (2001) Curr opin Mol Ther 2001 3:15-24; WO96/02555, WO98/16247, WO98/18810, WO98/40100, WO98/55495, WO98/37919 and WO98/52581 etc.
[25] WO99/52549.
[26] WO01/21207.
[27] WO01/21152.
[28] WO00/62800.
[29] WO00/23105.
[30] WO99/11241.
[31] WO98/57659.
[32] Del Giudice et al. (1998) Molecular Aspects of Medicine, vol. 19, number 1.
[33] Johnson et al. (1999) Bioorg Med Chem Lett 9:2273-2278.
[34] International patent application WO00/50078.
[35] Singh et al. (2001) J. Cont. Rele. 70:267-276.
[36] Covacci & Rappuoli (2000) J. Exp. Med 19:587-592.
[37] WO93/18150.
[38] Covacci et al. (1993) Proc. Natl. Acad. Sci. USA 90: 5791-5795.

[39] Tummuru et al. (1994) *Infect. Immun.* 61:1799-1809.
[40] Marchetti et al. (1998) *Vaccine* 16:33-37.
[41] Telford et al. (1994) *J. Exp. Med.* 179:1653-1658.
[42] Evans et al. (1995) *Gene* 153:123-127.
[43] WO96/01272 & WO96/01273, especially SEQ ED NO:6.
[44] WO97/25429.
[45] WO98/04702.
[46] WO99/24578.
[47] WO99/36544.
[48] WO99/57280.
[49] WO00/22430.
[50] Tettelin et al. (2000) *Science* 287:1809-1815.
[51] WO96/29412.
[52] Pizza et al. (2000) *Science* 287:1816-1820.
[53] WO01/52885.
[54] Bjune et al. (1991) *Lancet* 338(8775):1093-1096.
[55] Fukasawa et al. (1999) *Vaccine* 17:2951-2958.
[56] Rosenqvist et al. (1998) *Dev. Biol. Stand.* 92:323-333.
[57] Costantino et al. (1992) *Vaccine* 10:691-698.
[58] Costantino et al. (1999), *Vaccine* 17:1251-1263.
[59] Watson (2000) *Pediatr Infect Dis J* 19:331-332.
[60] Rubin (2000) *Pediatr Clin North Am* 47:269-285, v.
[61] Jedrzejas (2001) *Microbiol Mol Biol Rev* 65:187-207.
[62] Bell (2000) *Pediatr Infect Dis J* 19:1187-1188.
[63] Iwarson (1995) *APMIS* 103:321-326.
[64] Gerlich et al. (1990) *Vaccine* 8 Suppl:S63-68 & 79-80.
[65] Hsu et al. (1999) *Clin Liver Dis* 3:901-915.
[66] Gustafsson et al. (1996) *N. Engl. J. Med.* 334:349-355.
[67] Rappuoli et al. (1991) *TIBTECH* 9:232-238.
[68] *Vaccines* (1988) eds. Plotkin & Mortimer. ISBN 0-7216-1946-0.
[69] Del Guidice et al. (1998) *Molecular Aspects of Medicine* 19:1-70.
[70] WO02/02606.
[71] Kalman et al. (1999) *Nature Genetics* 21:385-389.
[72] Read et al. (2000) *Nucleic Acids Res* 28:1397-406.
[73] Shirai et al. (2000) *J. Infect. Dis.* 181(Suppl 3):S524-S527.
[74] WO99/27105.
[75] WO00/27994.
[76] WO00/37494.
[77] WO99/28475.
[78] Ross et al. (2001) *Vaccine* 19:4135-4142.
[79] Sutter et al. (2000) *Pediatr Clin North Am* 47:287-308.
[80] Zimmerman & Spann (1999) *Am Fam Physician* 59:113-118, 125-126.
[81] Dreesen (1997) *Vaccine* 15 Suppl:S2-6.
[82] *MMWR Morb Mortal Wkly Rep* 1998 Jan. 16; 47(1):12, 19.
[83] McMichael (2000) *Vaccine* 19 Suppl 1:S101-107.
[84] Schuchat (1999) *Lancet* 353(9146):51-6.
[85] WO02/34771.
[86] Dale (1999) *Infect Dis Clin North Am* 13:227-43, viii.
[87] Ferretti et al. (2001) *PNAS USA* 98: 4658-4663.
[88] Kuroda et al. (2001) *Lancet* 357(9264):1225-1240; see also pages 1218-1219.
[89] *J Toxicol Clin Toxicol* (2001) 39:85-100.
[90] Demicheli et al. (1998) *Vaccine* 16:880-884.
[91] Stepanov et al. (1996) *J Biotechnol* 44:155-160.
[92] Ingram (2001) *Trends Neurosci* 24:305-307.
[93] Rosenberg (2001) *Nature* 411:380-384.
[94] Moingeon (2001) *Vaccine* 19:1305-1326.
[95] Robinson & Torres (1997) *Seminars in Immunology* 9:271-283.
[96] Donnelly et al. (1997) *Annu Rev Immunol* 15:617-648.
[97] Scott-Taylor & Dalgleish (2000) *Expert Opin Investig Drugs* 9:471-480.
[98] Apostolopoulos & Plebanski (2000) *Curr Opin Mol Ther* 2:441-447.
[99] Ilan (1999) *Curr Opin Mol Ther* 1:116-120.
[100] Dubensky et al. (2000) *Mol Med* 6:723-732.
[101] Robinson & Pertmer (2000) *Adv Virus Res* 55:1-74.
[102] Donnelly et al. (2000) *Am J Respir Crit Care Med* 162(4 Pt 2):S190-193.
[103] Davis (1999) *Mt. Sinai J. Med.* 66:84-90.

The invention claimed is:

1. A saccharide of the formula:

wherein:

T is of the formula (A) or (B):

n is integer from 1 to 100;

each Z group is independently selected from —OH, —OAc, —OC(O)N(R$^1$)-L-M or —OC(O)N(R$^1$)-L-C(O)H;

each Q group is independently selected from —OH, —OAc, —OC(O)N($R^1$)-L-M or —OC(O)N($R^1$)-L-C(O)H;

W is selected from —OH, —OAc, —OC(O)N($R^1$)-L-M or —OC(O)N($R^1$)-L-C(O)H;

V is —N($R^1$)-L-M or —N($R^1$)-L-C(O)H;

wherein $R^1$ is selected from H or $C_1$-$C_6$ alkyl, L is a $C_1$-$C_{12}$ alkylene group and M is a masked aldehyde group, and provided that the saccharide comprises at least one moiety of the formula —N($R^1$)-L-M, —N($R^1$)-L-C(O)H, —OC(O)N($R^1$)-L-M or —OC(O)N($R^1$)-L-C(O)H.

2. The saccharide of claim 1 wherein n is an integer from 15 to 25.

3. The saccharide of claim 1 wherein T is of the formula (A).

4. The saccharide of claim 1 wherein Q and Z are a mixture of OH and OAc groups in essentially the same relative proportions as in the native *Neisseria meningitidis* serogroup A saccharide, with the exception that one of the Q or Z groups is —OC(O)N($R^1$)-L-M or —OC(O)N($R^1$)-L-C(O)H.

5. The saccharide of claim 4 wherein one of the Q groups is —OC(O)N($R^1$)-L-M or —OC(O)N($R^1$)-L-C(O)H.

6. A process for modifying a capsular saccharide comprising the steps of:
(a) providing a capsular saccharide having a hydroxyl group;
(b) reacting the hydroxyl group with a bifunctional reagent in an organic solvent;
(c) reacting the product of step (b) with an amino compound of formula (III):

$$HN(R^1)\text{-L-M} \qquad (III)$$

wherein $R^1$ is selected from H or $C_1$-$C_6$ alkyl, L is a $C_1$-$C_{12}$ alkylene group and M is a masked aldehyde group.

7. The process of claim 6 wherein the capsular saccharide is *Neisseria meningitidis* serogroup A saccharide.

8. The process of claim 6, wherein the organic solvent is an aprotic solvent.

9. The process of claim 8 wherein the aprotic solvent is selected from dimethylsulfoxide (DMSO), dimethylformamide (DMF), formamide, hexamethylphosphoramide (HMPA), hexamethylphosphorus triamide (HMPT), 1,3-dimethyl-3,4,5,6-tetrahydro-2(1H)-pyrimidinone (DMPU) or dimethylacetamide (DMAC).

10. The process of claim 8 wherein the aprotic solvent is DMSO.

11. The process of claim 6 wherein the bifunctional reagent is selected from 1,1'-carbonyldiimidazole (CDI), carbonyl di-1,2,4-triazole (CDT), carbonyl di-1,2,3-benzotriazole (CDB), diphenylcarbonate, cyanogen bromide, phosgene or triphosgene.

12. The process of claim 11 wherein the bifunctional reagent is CDI.

13. The process of claim 6 wherein the amino compound in step (c) is $H_2N(CH_2)_3CH(OH)CH_2OH$.

14. The process of claim 6, further comprising the step of (d) unmasking the masked aldehyde group M, thereby providing an aldehyde compound.

15. The process of claim 14 wherein the masked aldehyde group M is —CH(OH)$CH_2$OH and the unmasking step is a periodate cleavage.

16. The process of claim 14, further comprising the step of (e) linking the aldehyde compound to a protein by a reductive amination reaction.

17. The process of claim 16 wherein the reducing agent in the reductive amination reaction is $NaBH_3CN$.

18. A process for modifying a *Neisseria meningitidis* serogroup A saccharide comprising the steps of:
(a) providing a *Neisseria meningitidis* serogroup A saccharide;
(b) reacting a hydroxyl group on the saccharide with CDI in DMSO solvent;
(c) reacting the product of step (b) with $H_2N(CH_2)_3CH(OH)CH_2OH$;
(d) cleaving the product of step (c) with periodate, thereby providing an aldehyde compound; and
(e) linking the aldehyde compound of step (d) to a protein by a reductive amination reaction using $NaBH_3CN$.

19. A saccharide-protein conjugate wherein the saccharide and protein moieties are linked via a group of formula (IV):

$$\text{A-N}(R^1)\text{-L-NH—} \qquad (IV)$$

wherein A is a bond, —C(O)— or —OC(O)—; $R^1$ is selected from H or $C_1$-$C_6$ alkyl; and L is a $C_1$-$C_{12}$ alkylene group.

20. A saccharide-protein conjugate of claim 19 wherein $R^1$ is H, A is —OC(O)— and L is —$(CH_2)_4$—.

21. The conjugate of claim 19 wherein the saccharide is a *Neisseria meningitidis* serogroup A saccharide.

22. The conjugate of claim 19 wherein the protein is a bacterial toxin or toxoid.

23. The conjugate of claim 22 wherein the bacterial toxin or toxoid is diphtheria toxin or toxoid.

24. The conjugate of claim 22 wherein the bacterial toxin or toxoid is $CRM_{197}$.

25. A pharmaceutical composition comprising the saccharide-protein conjugate of claim 19 and a pharmaceutically acceptable carrier.

26. The composition of claim 25, further comprising a vaccine adjuvant.

27. The composition of claim 26, which is a vaccine against a disease caused by *Neisseria meningitidis*.

28. A method for raising an antibody response in a mammal, comprising administering the pharmaceutical composition of claim 25 to the mammal.

29. A method for immunising a mammal comprising administering to the mammal the pharmaceutical composition of claim 25.

* * * * *